United States Patent
Noble et al.

(10) Patent No.: US 10,302,585 B2
(45) Date of Patent: May 28, 2019

(54) CAPACITIVE DOE INTEGRITY MONITOR

(71) Applicant: APPLE INC., Cupertino, CA (US)

(72) Inventors: Hannah D. Noble, Sunnyvale, CA (US); Kevin A. Sawyer, Cupertino, CA (US); Martin B. Adamcyk, Burlingame, CA (US); Yazan Z. Alnahhas, Mountain View, CA (US); Yu Qiao Qu, Portola Valley, CA (US); Moshe Kriman, Tel Aviv (IL); Adar Magen, Herzliya Pituach (IL)

(73) Assignee: APPLE INC., Cupertino, CA (US)

( * ) Notice: Subject to any disclaimer, the term of this patent is extended or adjusted under 35 U.S.C. 154(b) by 241 days.

(21) Appl. No.: 15/272,454

(22) Filed: Sep. 22, 2016

(65) Prior Publication Data

US 2017/0199144 A1    Jul. 13, 2017

Related U.S. Application Data

(60) Provisional application No. 62/275,810, filed on Jan. 7, 2016, provisional application No. 62/331,465, filed on May 4, 2016.

(51) Int. Cl.
*G01N 27/00* (2006.01)
*G02B 27/44* (2006.01)
(Continued)

(52) U.S. Cl.
CPC ....... *G01N 27/24* (2013.01); *B29D 11/00807* (2013.01); *G02B 1/12* (2013.01);
(Continued)

(58) Field of Classification Search
CPC ...... G01N 27/24; G02B 27/425; G02B 27/42; G02B 27/62; G02B 27/4272; G02B 27/4277
See application file for complete search history.

(56) References Cited

U.S. PATENT DOCUMENTS 7,146,076 B2 *  12/2006  Fujieda ................. G02F 1/292
                                                    385/37
8,027,089 B2 *   9/2011  Hayashi .............. B81C 99/0085
                                                    359/566
(Continued)

FOREIGN PATENT DOCUMENTS

EP        0800643 A1    10/1997

OTHER PUBLICATIONS

International Application # PCT/US2016/065478 Search Report dated Mar. 28, 2017.
(Continued)

*Primary Examiner* — Minh N Tang
(74) *Attorney, Agent, or Firm* — Kligler & Associates

(57) ABSTRACT

An optical module includes first and second transparent substrates and a spacer between the first and second transparent substrates, holding the first transparent substrate in proximity to the second transparent substrate, with first and second diffractive optical elements (DOEs) on respective faces of the first and second transparent substrates. At least first and second capacitance electrodes are disposed respectively on the first and second transparent substrates in proximity to the first and second DOEs. Circuitry is coupled to measure changes in a capacitance between at least the first and second capacitance electrodes.

11 Claims, 15 Drawing Sheets

(51) Int. Cl.
  *G01N 27/24* (2006.01)
  *B29D 11/00* (2006.01)
  *G02B 1/12* (2006.01)
  *G02B 27/42* (2006.01)
  *G02B 27/62* (2006.01)
  *B29K 63/00* (2006.01)

(52) U.S. Cl.
  CPC ..... *G02B 27/4272* (2013.01); *G02B 27/4277* (2013.01); *G02B 27/62* (2013.01); *B29K 2063/00* (2013.01); *B29K 2995/0005* (2013.01); *B29K 2995/0018* (2013.01)

(56) References Cited

U.S. PATENT DOCUMENTS

| | | |
|---|---|---|
| 9,091,413 B2 | 7/2015 | Petronius et al. |
| 2002/0024734 A1 | 2/2002 | Nakabayashi |
| 2002/0163725 A1 | 11/2002 | Kobayashi |
| 2003/0042688 A1 | 3/2003 | Davie et al. |
| 2008/0211978 A1 | 9/2008 | Hikmet et al. |
| 2008/0240502 A1 | 10/2008 | Freedman et al. |
| 2009/0185274 A1 | 7/2009 | Shpunt |
| 2012/0013880 A1 | 1/2012 | Choi et al. |
| 2012/0223218 A1 | 9/2012 | Miyasaka |
| 2015/0070032 A1 | 3/2015 | Strocchia-Rivera |

OTHER PUBLICATIONS

CN Utility Model Patent ZL201720007435.8 Patentability Evaluation Report dated Sep. 29, 2017.

\* cited by examiner

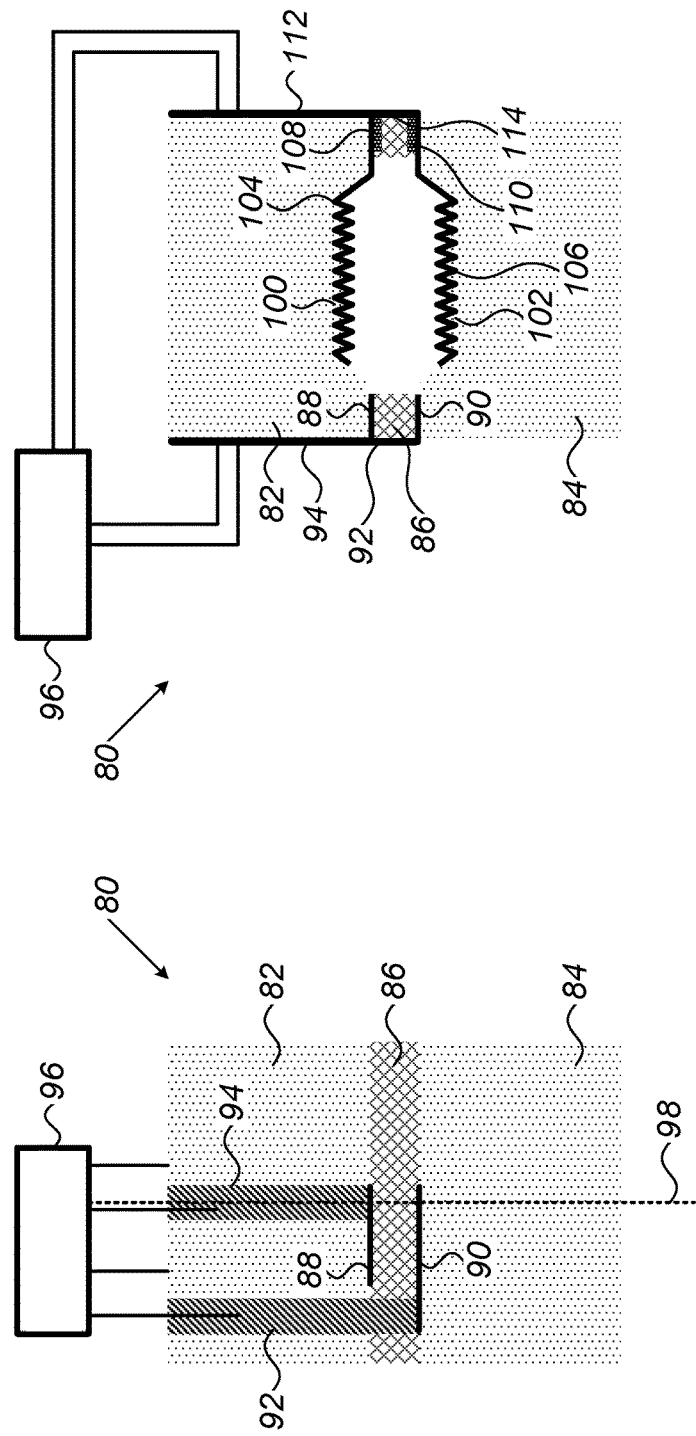

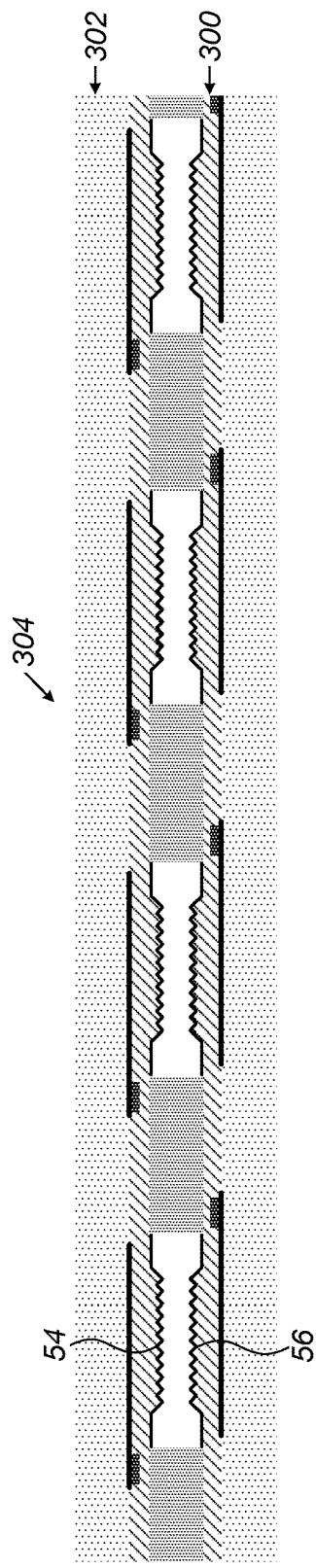
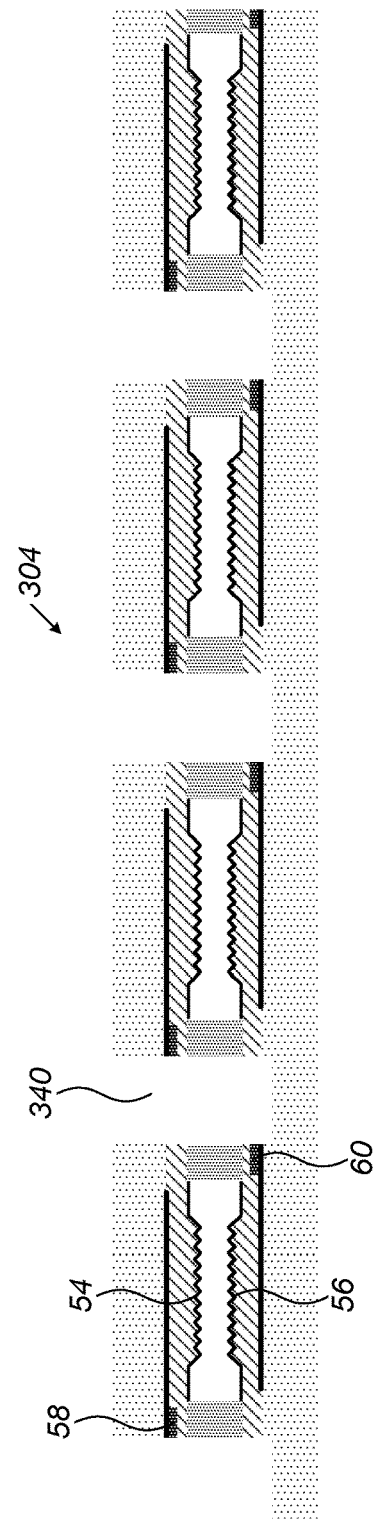
FIG. 6H
FIG. 6I

CAPACITIVE DOE INTEGRITY MONITOR

CROSS-REFERENCE TO RELATED APPLICATION

This application claims the benefit of U.S. Provisional Patent Application 62/275,810, filed Jan. 7, 2016, and U.S. Provisional Patent Application 62/331,465, filed May 4, 2016, which are incorporated herein by reference.

FIELD OF THE INVENTION

The present invention relates generally to diffractive optics, and particularly to monitoring the performance of a diffractive optical element (DOE).

BACKGROUND

Optical modules are very commonly used in consumer electronic devices. For example, almost all current portable telephones and computers include a miniature camera module. Miniature optical projection modules are also expected to come into increasing use in portable consumer devices for a variety of purposes.

Such projection modules may be used, for example, to cast a pattern of structured light onto an object for purposes of 3D mapping (also known as depth mapping). In this regard, U.S. Patent Application Publication 2008/0240502 describes an illumination assembly in which a light source, such as a laser diode or LED, transilluminates a transparency with optical radiation so as to project a pattern onto the object. (The terms "optical" and "light" as used in the present description and in the claims refer generally to any and all of visible, infrared, and ultraviolet radiation.) An image capture assembly captures an image of the pattern that is projected onto the object, and a processor processes the image so as to reconstruct a three-dimensional (3D) map of the object.

Optical projectors may, in some applications, project light through one or more diffractive optical elements (DOEs). For example, U.S. Patent Application Publication 2009/0185274 describes apparatus for projecting a pattern that includes two DOEs, which are together configured to diffract an input beam so as to at least partially cover a surface. The combination of DOEs reduces the energy in the zero-order (undiffracted) beam. In one embodiment, the first DOE generates a pattern of multiple beams, and the second DOE serves as a pattern generator to form a diffraction pattern on each of the beams.

As another example, U.S. Pat. No. 9,091,413 describes photonics modules that include optoelectronic components and optical elements (refractive and/or patterned) in a single integrated package. According to the inventors, these modules can be produced in large quantities at low cost, while offering good optical quality and high reliability. They are useful as projectors of patterned light, for example in 3D mapping applications as described above, but they may also be used in various other applications that use optical projection and sensing, including free-space optical communications.

SUMMARY

Embodiments of the present invention that are described hereinbelow provide capacitive monitoring for the integrity of diffractive optical elements (DOE).

There is therefore provided, in accordance with an embodiment of the invention, an optical module, including first and second transparent substrates, a spacer between the first and second transparent substrates, holding the first transparent substrate in proximity to the second transparent substrate, and first and second diffractive optical elements (DOEs) on respective faces of the first and second transparent substrates. At least first and second capacitance electrodes are disposed respectively on the first and second transparent substrates in proximity to the first and second DOEs. Circuitry is coupled to measure changes in a capacitance between at least the first and second capacitance electrodes.

In a disclosed embodiment, the module includes conductive shielding coatings on one or more outer surfaces of the transparent substrates.

In one embodiment, the first and second capacitance electrodes include planar electrodes. In an alternative embodiment, the first and second capacitance electrodes include interdigitated electrodes.

In a disclosed embodiment, the module includes electrical conductors including conductive epoxy, which are deposited on one or more side surfaces of the transparent substrates and couple the circuitry to the first and second capacitance electrodes. Alternatively or additionally, the module includes electrical conductors that are deposited inside one or more vias passing through the transparent substrates and couple the circuitry to the first and second capacitance electrodes.

In some embodiments, the module includes at least one additional pair of reference capacitance electrodes in a location insensitive to changes in the DOEs, wherein the circuitry is additionally coupled to the reference capacitance electrodes and is configured to compare the changes measured in the capacitance measured between the first and second capacitance electrodes to a reference capacitance value read from the reference capacitance electrodes.

In some embodiments, the spacer forms a hermetic seal between the first and second transparent substrates. Additionally or alternatively, the spacer includes an electrically conductive material, which is connected to ground potential.

In one embodiment, the electrodes are deposited on the respective faces of the substrate, and the DOEs are formed over the electrodes. Alternatively, the electrodes are deposited over the DOEs.

There is also provided, in accordance with an embodiment of the invention, a method for producing an optical module. The method includes providing first and second transparent substrates and forming first and second DOEs on respective faces of the first and second transparent substrates. First and second transparent conducting electrodes are formed over the first and second transparent substrates, respectively, such that the DOEs and electrodes are in mutual proximity. The first and second transparent substrates are bonded together to form a bonded substrate pair in which the first and second DOEs are in mutual alignment, with the first transparent substrate in proximity to and parallel to the second transparent substrate. Circuitry is coupled to measure a capacitance between the first and second capacitance electrodes.

In some embodiments, forming the first and second DOEs includes forming first and second arrays of the DOEs on the first and second transparent substrates, and the method includes dicing the bonded substrate pair into singulated modules, wherein each module includes a pair of DOEs in mutual alignment. In one embodiment, forming the first and second transparent conducting electrodes includes depositing and patterning the transparent conducting electrodes on the transparent substrates, wherein forming the first and second arrays of the DOEs includes depositing a transparent material over the transparent conducting electrodes, and forming the DOEs in the transparent material. Alternatively, forming first and second arrays of the DOEs includes etching or embossing the DOEs into the transparent substrates, and forming the first and second transparent conducting electrodes includes depositing and patterning the transparent conducting electrodes over the DOEs.

In some embodiments, coupling the circuitry includes depositing on the transparent substrates conductors connecting to the transparent conducting electrodes. The bonded substrate pair is partially diced so as to expose the conductors. A metal filt is deposited and patterned over the cuts generated by the partial dicing, so as to form a metal film connecting separately to each conductor.

Additionally or alternatively, dicing the bonded substrate pair includes cutting the bonded substrate pair into strips, wherein each strip includes a row of facing pairs of DOEs, and wherein conductors connecting to the transparent conducting electrodes on the transparent substrates are exposed by the cut. Each strip is turned by 90° along its long edge, and the turned strips are stacked side-by-side with the exposed conductors accessible on a side of the stacked strips. Coupling the circuitry includes depositing and patterning conductive epoxy over the side of the strips, connecting to each of the exposed conductors, before completing the dicing of the strips.

There is additionally provided, in accordance with an embodiment of the invention, a method for operating an optical module. The method includes measuring a capacitance between electrodes on transparent substrates in the optical module in proximity to diffractive optical elements (DOEs) disposed on the substrates. A malfunction of the optical module is detected responsively to a change in the measured capacitance.

The present invention will be more fully understood from the following detailed description of the embodiments thereof, taken together with the drawings in which:

BRIEF DESCRIPTION OF THE DRAWINGS

FIGS. 2A-B are schematic side and sectional views of a DOE module, in accordance with another embodiment of the invention;

FIGS. 6A-K are schematic sectional and top views of a substrate showing successive steps in a process of manufacturing a DOE module on the substrate, in accordance with another embodiment of the invention;

DETAILED DESCRIPTION OF EMBODIMENTS

Figure 1A:
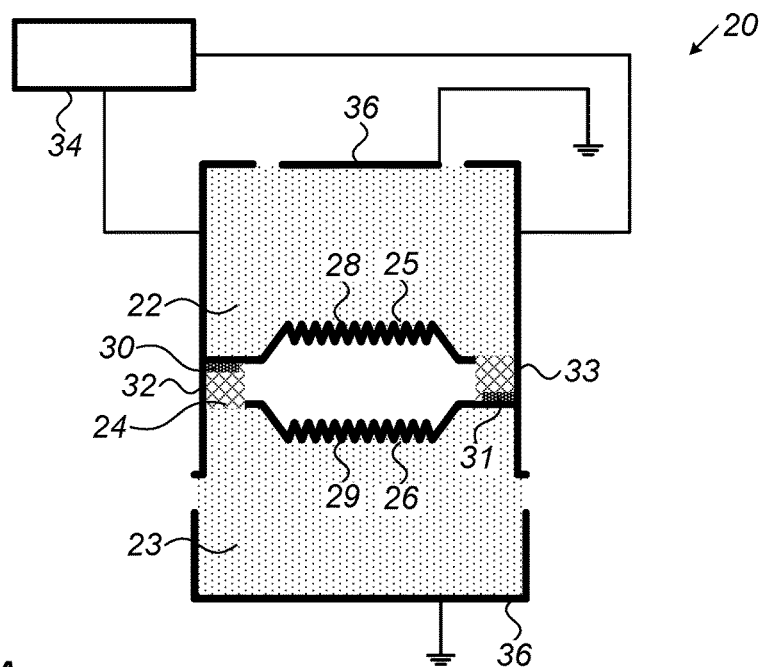
FIGS. 1A-B are schematic sectional views of DOE modules with capacitive sensors, in accordance with two embodiments of the invention.

Mass production of miniaturized optical devices calls for product designs that meet the often-conflicting objectives of high precision and reliability and low manufacturing cost. For example, a miniature projection module may be configured to project a structured light pattern, and images of the pattern captured by a camera module may then be processed for purposes of depth mapping. For accurate depth mapping, it is important that the contrast and geometry of the pattern be consistent and well controlled.

At the same time, consumer devices are expected to function in a wide range of different temperatures and environmental conditions. Temperature variations cause components of the optical modules to expand and contract, leading to changes in focal properties. Thermal swings can particularly degrade the performance of projection optics in structured light projection modules, leading to reduced resolution, range and accuracy of systems that are built on such modules. This problem is particularly acute when the optical components of the module include refractive or diffractive elements made from molded plastic (dictated by the need for mass production at low cost), because such elements are particularly prone to thermal expansion and contraction.

Another issue that can affect the performance of projection modules in consumer electronic devices is loss of mechanical integrity. For example, if a mechanical or thermal shock causes the patterning element in a projection module, such as a diffractive optical element or other patterned transparency, to break, become detached, or shift out of place, the module may emit an intense, highly focused beam, rather than a structured pattern as intended. Similar effects on the mechanical integrity may be caused by humidity. Moreover, high humidity may lead to the condensation of water droplets on the surface of the DOEs, leading to a change in their optical characteristics.

Embodiments of the present invention that are described herein address these problems by incorporating one or more capacitive sensors into the structure of the DOE. These capacitive sensors are sensitive to the mechanical integrity and dimensional changes of the DOE as well as condensation within the DOE, and will, when interrogated by a control circuit, provide information about the deviation of the DOE from its normal mechanical, dimensional, and optical state. This information can be further utilized to ascertain proper functioning of the DOE, and, where necessary, turn off the primary radiation source illuminating the DOE.

In an embodiment, the capacitance between the electrodes of the capacitive sensor is measured based on the mutual capacitance: In the case of a capacitive sensor comprising two opposing electrodes, one of the electrodes functions as a drive electrode, and the other electrode functions as a sense electrode. Changes in the structure of the DOE will result in changes of the mutual capacitance, which will generally be indicative of a mechanical or optical failure in the optical module (referred to hereinafter as a DOE module). The mutual capacitance can also change as the result of a corruption of the assembly due to other causes, such as a water droplet, condensation, or other contaminants on a DOE surface.

In some embodiments of the present invention, the DOE module comprises at least one pair of reference capacitance electrodes in a location of the DOE module that is not affected by changes in the DOEs. These measurements are used as a reference for differential capacitance measurements, thus reducing the impact of environmental effects, e.g. thermal changes and parasitic capacitances, on the capacitance measurements probing the DOE integrity.

In a further embodiment, conductive shield electrodes, connected to ground potential, are deposited on outside surfaces of the DOE module, for reducing the effects of external electric fields on the capacitance measurements probing the DOE integrity. In a still further embodiment, the conductive shield electrodes are formed on the inside surfaces of DOE module, separated from the capacitance electrodes by an insulating layer.

Figure 1B:
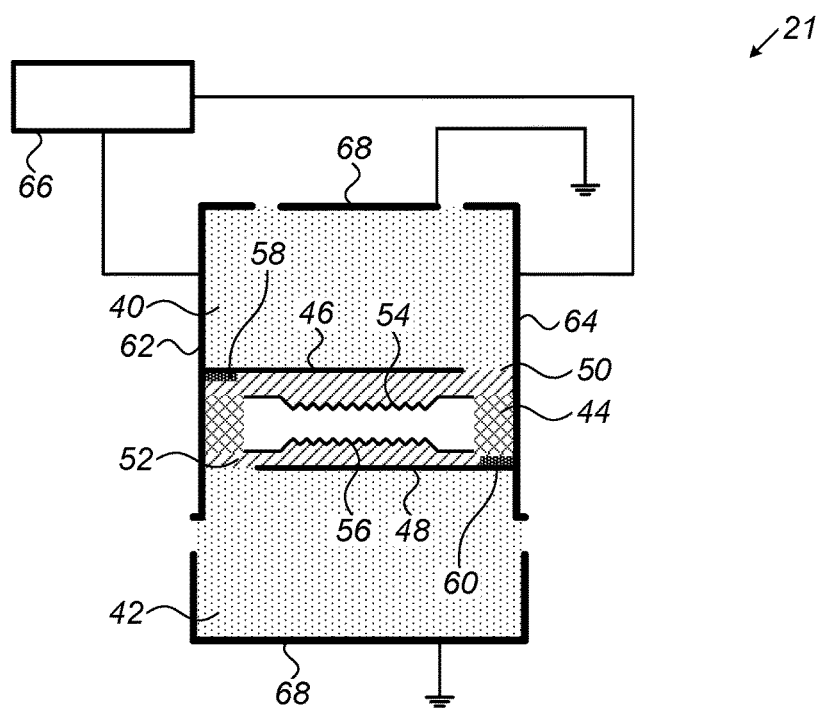

FIGS. 1A-B are schematic sectional views of DOE modules 20 and 21 with capacitive sensors, in accordance with two embodiments of the invention. These two embodiments differ in terms of the mutual positioning of the DOEs and the capacitance electrodes, as will be described in detail below.

FIG. 1A shows a schematic sectional view of DOE module 20, comprising two transparent substrates 22 and 23, typically made out of glass or plastic, separated by spacer 24. Although spacer 24 is seen in the sectional view in two locations, it can comprise either one continuous piece or multiple pieces. Two DOEs 25 and 26 are formed on the two inside surfaces of substrates 22 and 23 by etching, embossing, or another process known to persons skilled in the art. First and second capacitance electrodes 28 and 29 are deposited over DOEs 25 and 26, and are connected to internal conductors 30 and 31, positioned on substrates 22 and 23, which in turn are connected to external conductors 32 and 33 outside substrates 22 and 23. External conductors 32 and 33 are further connected to a capacitance measurement circuit 34.

The outer surfaces of transparent substrates 22 and 23 are typically coated with a transparent, electrically conductive thin film 36, distinct and isolated from external conductors 32 and 33, which is connected to ground potential, and which acts as a ground shield and assists in eliminating parasitic capacitances and noise. The electrically-conductive thin film is manufactured of ITO (Indium-Tin Oxide) or similar transparent, conductive material.

In an embodiment, spacer 24 between substrates 22 and 23 is manufactured of conductive material and is connected to ground potential for providing additional shielding. In another embodiment, spacer 24 is manufactured of an insulating material, such as a polymer or a glassy ceramic composition (for example, a frit), the latter being used to create a hermetic seal for the space between DOEs 25 and 26.

FIG. 1B shows a schematic sectional view of DOE module 21, comprising two transparent substrates 40 and 42, typically made out of glass or plastic, separated by spacer 44. As in FIG. 1A, spacer 44 comprises one continuous piece. First and second capacitance electrodes 46 and 48 are disposed on substrates 40 and 42, with overlying dielectric films 50 and 52, such as $SiO_2$ and/or polymer, over electrodes 46 and 48, with DOEs 54 and 56 formed in the dielectric films.

First and second capacitance electrodes 46 and 48 are connected to conductors 58 and 60, which in turn are connected to external conductors 62 and 64. External conductors 62 and 64 are further connected to a capacitance measurement circuit 66.

Similarly to the embodiment in FIG. 1A, the outer surfaces of transparent substrates 40 and 42 are typically coated with a uniform, transparent, electrically conductive thin film 68, connected to ground potential. In another embodiment, an electrically conductive thin film, connected to ground potential and functioning as a ground shield, is deposited between capacitance electrode 46 and substrate 40, as well as between capacitance electrode 48 and substrate 42. The ground shield is isolated from capacitance electrodes 46 and 48 by a thin layer of $SiO_2$ or similar insulation.

Further, similarly to the embodiments in FIG. 1A, in an embodiment, spacer 44 is manufactured of conductive material and is connected to ground potential for providing additional shielding. In another embodiment, spacer 44 is manufactured of an insulating material, such as a polymer or a glassy ceramic composition (frit), the latter being used for a hermetic seal for the space between DOEs 54 and 56.

FIGS. 2A-B show schematically an embodiment of the invention, wherein a DOE module 80 comprises reference capacitance electrodes 88 and 90.

FIG. 2A shows a side view of DOE module 80, comprising substrates 82 and 84, a spacer 86, a first reference capacitance electrode 88, and a second reference capacitance electrode 90. The electrodes are connected to external conductors 92 and 94, which are further connected to a capacitance measurement circuit 96.

FIG. 2B is a sectional view of DOE module 80, as seen if module 80 were cut along a line 98, with a cut perpendicular to the plane of FIG. 2A. This sectional view shows the same parts as in FIG. 2A: substrates 82 and 84, spacer 86, first and second reference capacitance electrodes 88 and 90, as well as external conductors 92 and (partially overlapping in the view of FIG. 2B). In addition, the sectional view shows—similarly to the embodiment shown in FIG. 1A—DOEs 100 and 102, first and second capacitance electrodes 104 and 106, and conductors 108 and 110 connecting to first and second capacitance electrodes 104 and 106 (in the current embodiment on the same side of the DOE module), as well as external conductors 112 and 114 (partially overlapping in the view of FIG. 2B) connecting to conductors 108 and 110 and further connecting to capacitance measurement circuit 96. Reference capacitance electrodes 88 and 90 are located on the two sides of spacer 86, and are physically separated from DOEs 100 and 102. Consequently, changes either in DOEs 100 or 102 or contamination in the air space between DOEs will have no effect on the capacitance between reference capacitance electrodes 88 and 90.

Capacitance measurement circuit 96 measures both the capacitance between first and second capacitance electrodes 104 and 106, and the capacitance between first and second reference capacitance electrodes 88 and 90. Capacitance measurement circuit 96 further compares the changes measured in the capacitance measured between first and second capacitance electrodes 104 and 106 to a reference capacitance value read from reference capacitance electrodes 88 and 90. This sort of differential capacitance measurement reduces the impact of environmental effects on the capacitance measurements that probe the DOE integrity.

Figure 3:
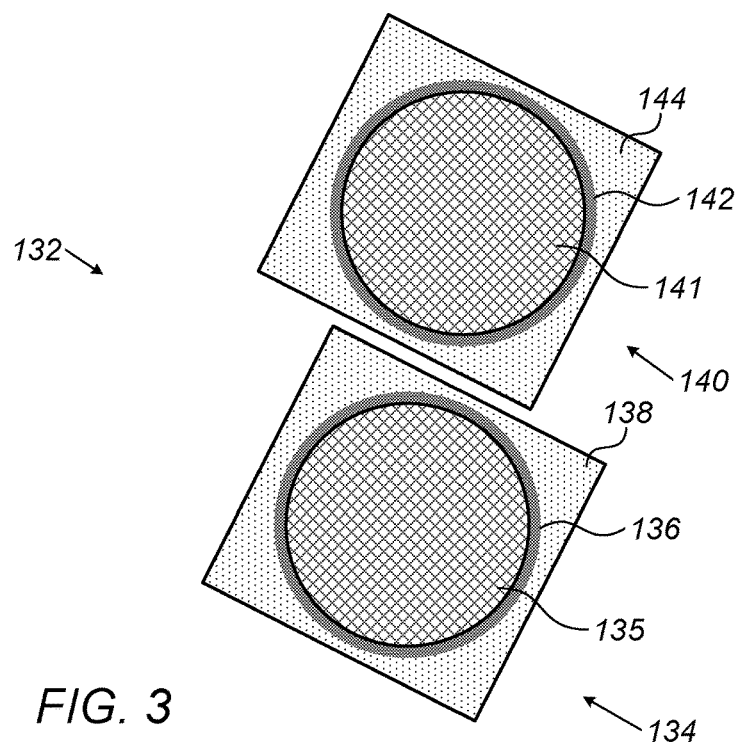
FIG. 3 is a schematic exploded view of a DOE module, in accordance with an embodiment of the invention.
Figure 4:
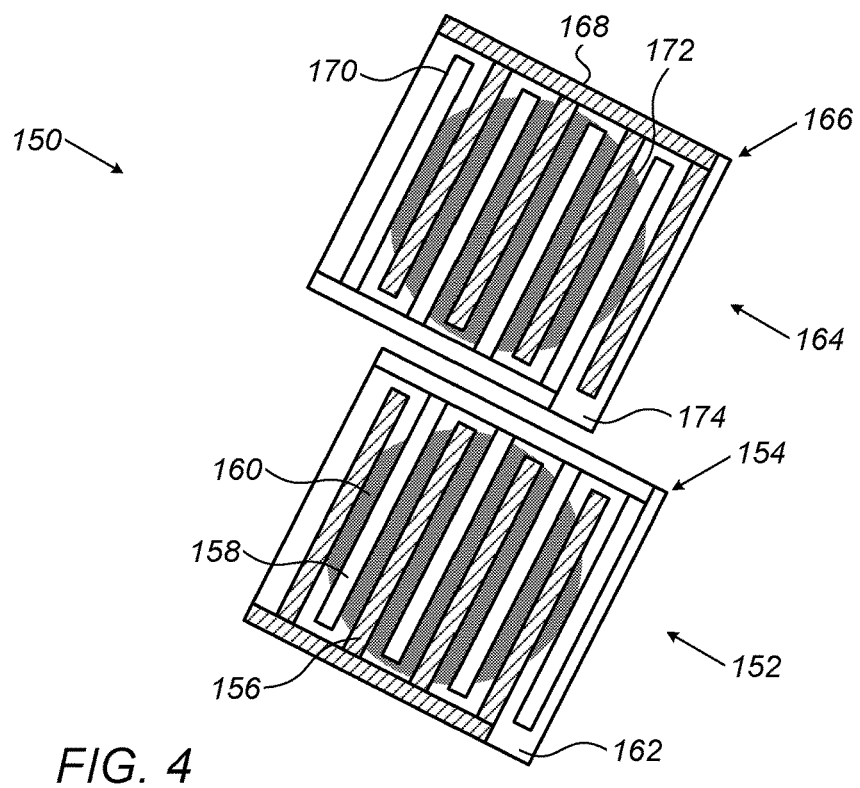
FIG. 4 is a schematic exploded view of a DOE module, in accordance with another embodiment of the invention.

FIGS. 3-4 are schematic views of embodiments of the invention, wherein two different capacitance measurement electrode schemes are shown: FIG. 3 shows planar electrodes 135 and 141, whereas FIG. 4 shows interdigitated electrodes 156, 158, 170 and 172. Each of the embodiments of planar electrodes and interdigitated electrodes may be realized based on either of the two different embodiments of capacitance electrode locations depicted in FIGS. 1A-B.

FIG. 3 is a schematic exploded view of the two halves of a DOE module 132, according to the electrode locations depicted in FIG. 1A. A bottom half 134 of DOE module 132 comprises a first capacitance electrode 135, formed over the air interface of a bottom DOE 136, which in turn is formed over a bottom substrate 138. A top half 140 of DOE module 132 comprises a second capacitance electrode 141, formed over the air interface of a top DOE 142, which is formed over a top substrate 144. In an embodiment, wherein mutual capacitance is measured, first capacitance electrode 135 is used as drive electrode, and second capacitance electrode 141 is used as sense electrode.

FIG. 4 is a schematic exploded view of the two halves of a DOE module 150, according to the electrode locations depicted in FIG. 1A. A bottom half 152 of DOE module 150 comprises a first capacitance electrode assembly 154, which comprises a drive electrode 156 and a sense electrode 158, interdigitated with respect to each other. First capacitance electrode assembly 154 is formed over the air interface of a bottom DOE 160 (seen between the digits of first capacitance electrode assembly 154), which in turn is formed over a bottom substrate 162. A top half 164 comprises a second capacitance electrode assembly 166, which comprises a drive electrode 168 and a sense electrode 170, interdigitated with respect to each other. Second capacitance electrode assembly 166 is formed over the air interface of a top DOE 172 (seen between the digits of second capacitance electrode assembly 166), which in turn is formed over a top substrate 174. When DOE module 150 is in its functional (unexploded) configuration, the first and second electrode assemblies 154 and 166 are aligned in such a way that drive electrode 156 is opposite sense electrode 170, and sense electrode 158 is opposite drive electrode 168.

In an embodiment of the invention, capacitance electrode assemblies 154 and 166 can be connected to drive and sense circuitry in the following configurations: a) the current of drive electrode 156 is sensed by sense electrode 170, b) the current of drive electrode 168 is sensed by sense electrode 158, c) the current of drive electrode 156 is sensed by sense electrode 158, and d) the current of drive electrode 168 is sensed by sense electrode 170. Configurations (a) and (b) measure capacitance changes between bottom half 152 and top half 164 of DOE module 150, whereas configuration (c) measures capacitance changes between the electrodes of electrode assembly 154, and configuration (d) measures capacitance changes between the electrodes of electrode assembly 166. Measuring capacitance changes between the electrodes of a given surface, such as in configuration (c) or (d), increases the sensitivity for detecting water films that do not bridge the gap between bottom half 152 and top half 164 of DOE assembly 150, but create a droplet localized on one surface only.

In an embodiment, the multiple capacitances of configurations (a)-(d) are measured simultaneously by using different stimulation waveforms for the different drive currents, and analyzing the sense currents using signal processing in order to determine the relative contributions from the drive currents. In another embodiment, time multiplexing is used for the drive currents, enabling differentiation between the sense currents caused by different drive currents. In a further embodiment, a combination of different simulation waveforms and time multiplexing are used.

Although FIGS. 3-4 show the electrodes laid out in particular patterns, electrodes in other patterns, such as a grid pattern, may alternatively be deposited on the DOEs or substrates with similar effect and are considered to be within the scope of the present invention.

Figure 5A:
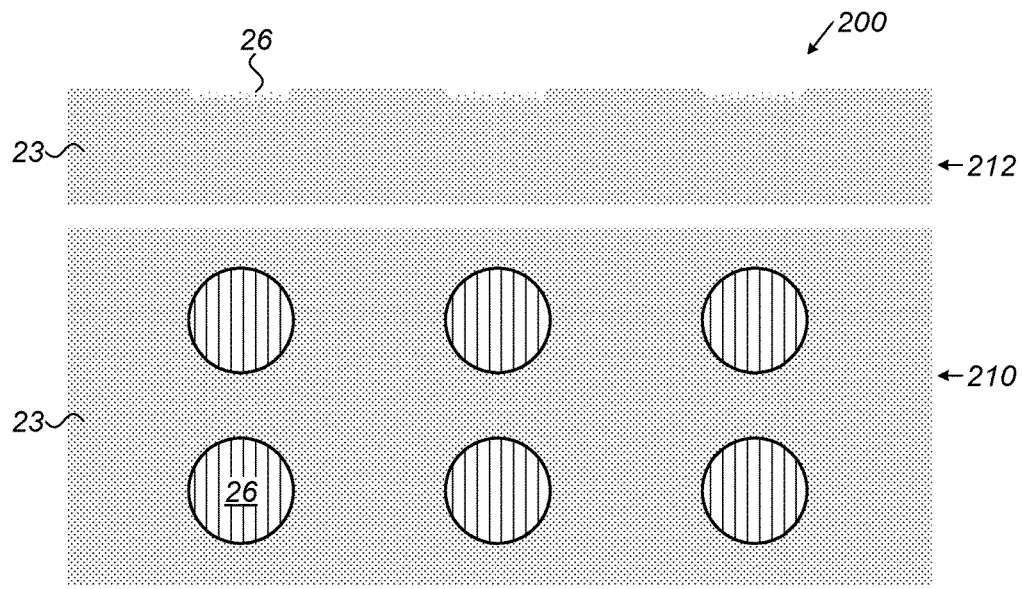
FIGS. 5A-K are schematic sectional and top views of a substrate showing successive steps in a process of manufacturing a DOE module on the substrate, in accordance with an embodiment of the invention.
Figure 5B:
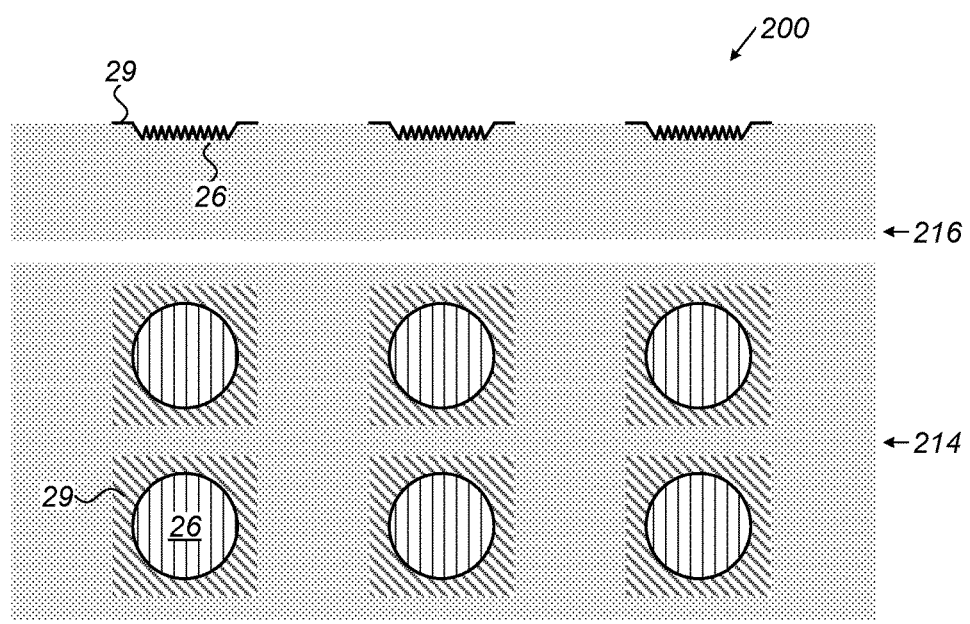
Figure 5C:
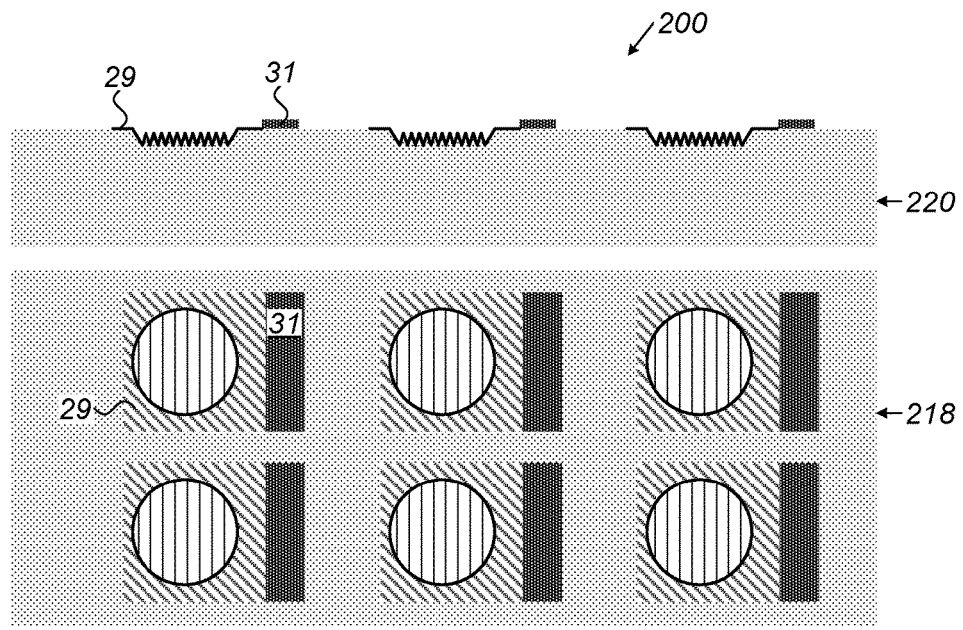
Figure 5D:
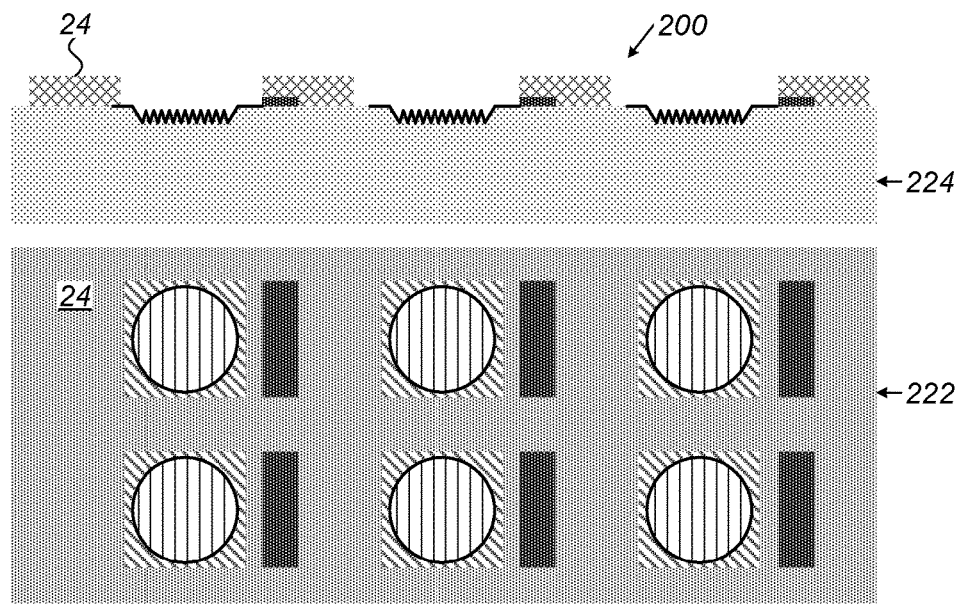
Figure 5E:
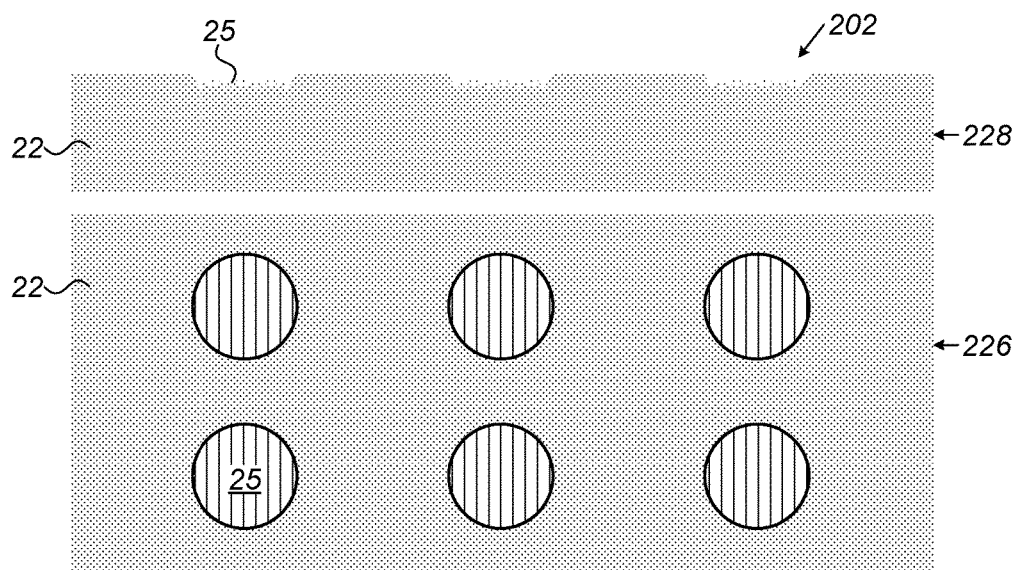
Figure 5F:
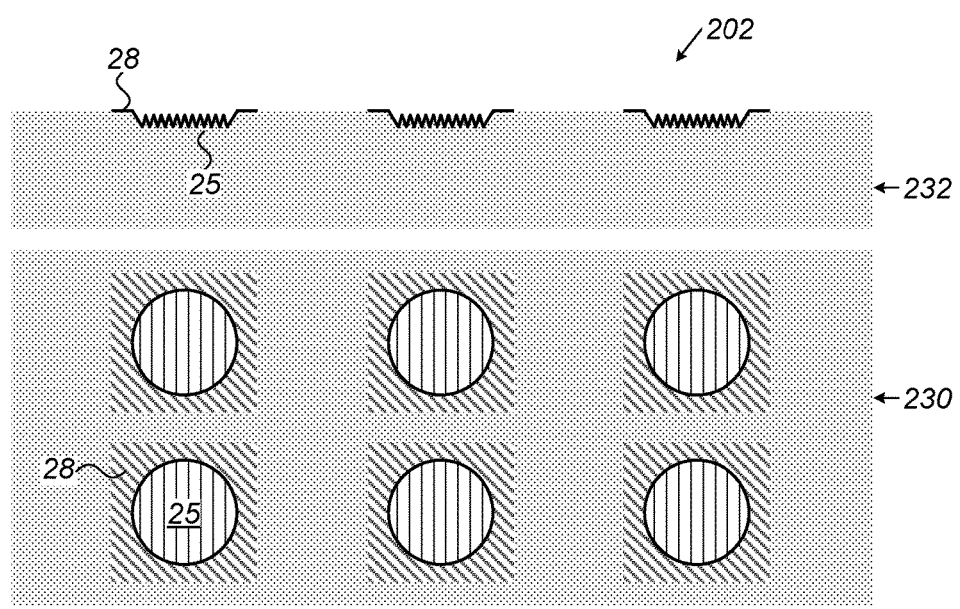
Figure 5G:
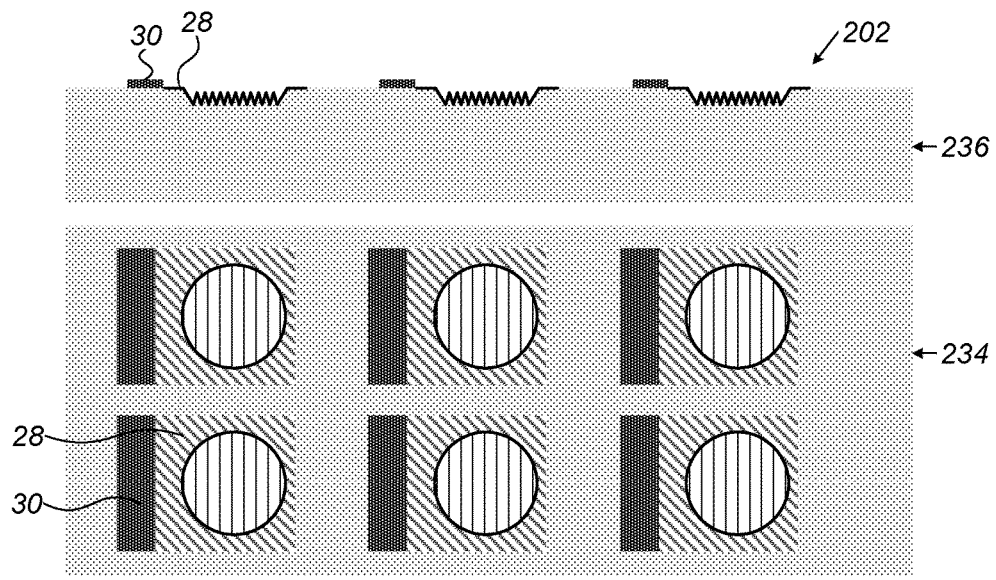
Figure 5H:
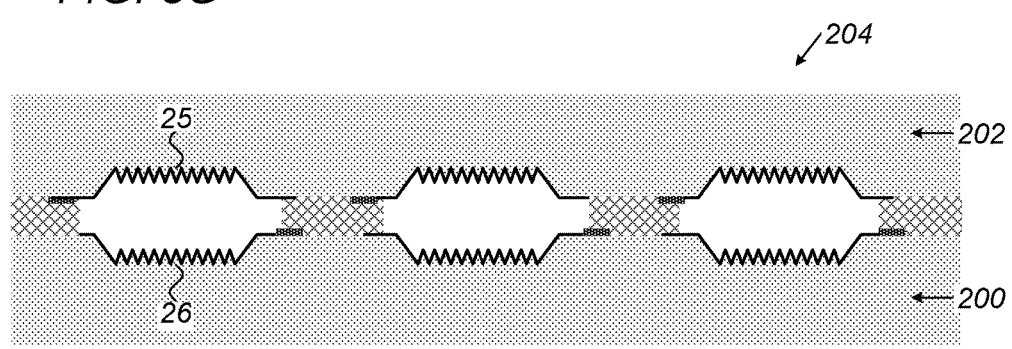
Figure 5I:
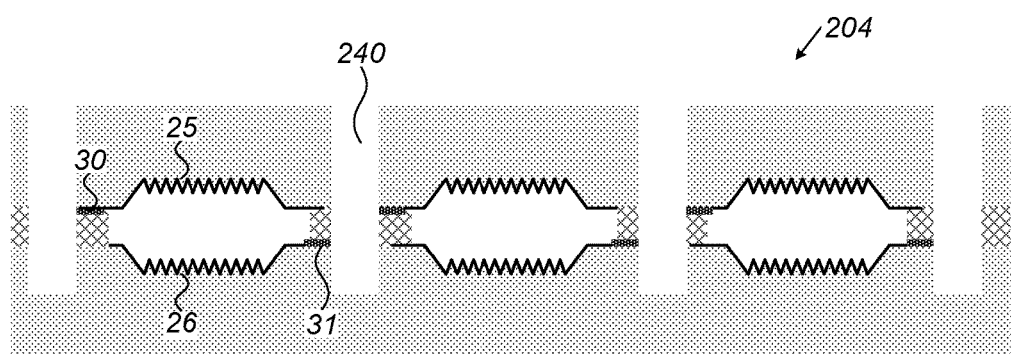
Figure 5J:
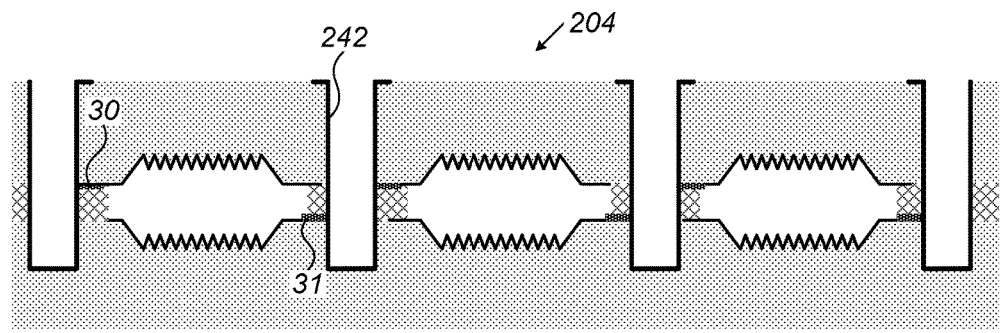
Figure 5K:
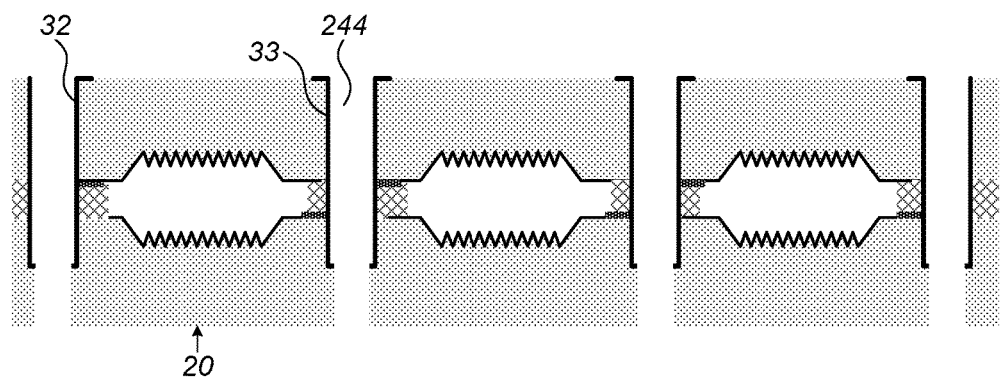

FIGS. 5A-J are schematic top and sectional views of substrates 22 and 23, showing successive steps in a manufacturing process, wherein first and second capacitance electrodes are deposited on the interfaces between DOEs and air, according to an embodiment of the invention. In this manufacturing process, whose end result has previously been depicted as DOE module 20 in FIG. 1A, two separate assemblies: an assembly 200 and an assembly 202, are built in sequential process steps, bonded together into an assembly 204, and then processed further. Although assemblies 200, 202, and 204 are modified throughout the process steps, we will keep this numbering of the assemblies from step to step in order to facilitate an understanding of the process. We will also use, where applicable, labels from FIG. 1A. FIG. 5A is a schematic view of an etching or embossing process step performed on assembly 200. FIGS. 5B-D are schematic views of coating and patterning steps performed on assembly 200. FIG. 5E is a schematic view of an etching or embossing process step performed on assembly 202. FIGS. 5F-G are schematic views of coating and patterning steps performed on assembly 202. FIGS. 5I-K are schematic views of process steps performed on assembly 204, after bonding of assemblies 200 and 202 into assembly 204 in FIG. 5H.

FIG. 5A shows a schematic top view 210 and a schematic sectional view 212 of the result of an etching or embossing process step for assembly 200. In this step, DOEs 26 have been etched or embossed into transparent substrate 23. Each DOE 26 forms a unit cell in the matrix of DOEs 26 on substrate 23, and subsequent process steps are performed in a parallel fashion to all unit cells of the matrix.

FIG. 5B shows a schematic top view 214 and a schematic sectional view 216 of the result of a coating and patterning step on assembly 200. In this process step, second capacitance electrodes 29 are coated and patterned over DOEs 26. Each second capacitance electrode 29 extends over DOE 26 and its close surroundings.

FIG. 5C shows a schematic top view 218 and a schematic sectional view 220 of the result the next coating and patterning step on assembly 200. In this coating and patterning step, conductors 31 are formed, connecting to second capacitance electrodes 29.

FIG. 5D shows a schematic top view 222 and a schematic sectional view 224 of the result of yet another coating and patterning step on assembly 200. In this coating and patterning step spacers 24 are formed. In another embodiment, spacers 24 are etched or embossed into the material of substrate 23.

FIG. 5E shows a schematic top view 226 and a schematic sectional view 228 of the result of an etching or embossing process step for assembly 202. In this step, DOEs 25 have been etched or embossed into transparent substrate 22. Similarly to assembly 200, each DOE 25 forms a unit cell in the matrix of DOEs 25 on substrate 22, and subsequent process steps are performed in a parallel fashion to all unit cells of the matrix.

FIG. 5F shows a schematic top view 230 and a schematic sectional view 232 of the result of a coating and patterning step on assembly 202. In this process step, first capacitance electrodes 28 are coated and patterned over DOEs 25. Each first capacitance electrode 28 extends over DOE 25 and its close surroundings.

FIG. 5G shows a schematic top view 234 and a schematic sectional view 236 of the result of another coating and patterning step on assembly 202. In this coating and patterning step, conductors 30 are formed, connecting to first capacitance electrodes 28.

FIG. 5H shows a schematic sectional view of assembly 204 formed by flipping assembly 202 over and bonding it to assembly 200. Assemblies 200 and 202 have been aligned so as to have each DOE 25 in assembly 202 facing DOE 26 in assembly 200.

FIG. 5I shows a schematic sectional view of assembly 204, after a partial dicing step that forms cuts 240 between consecutive pairs of DOEs 25 and 26, exposing the ends of conductors 30 and 31.

FIG. 5J shows a schematic sectional view of assembly 204, after metal deposition and patterning, forming metal films 242, connecting to conductors 30 and 31 through their exposed ends.

FIG. 5K shows a schematic sectional view, after dicing cuts 244 have separated assembly 204 into individual DOE modules 20, and have at the same time formed external conductors 32 and 33.

Figure 6A:
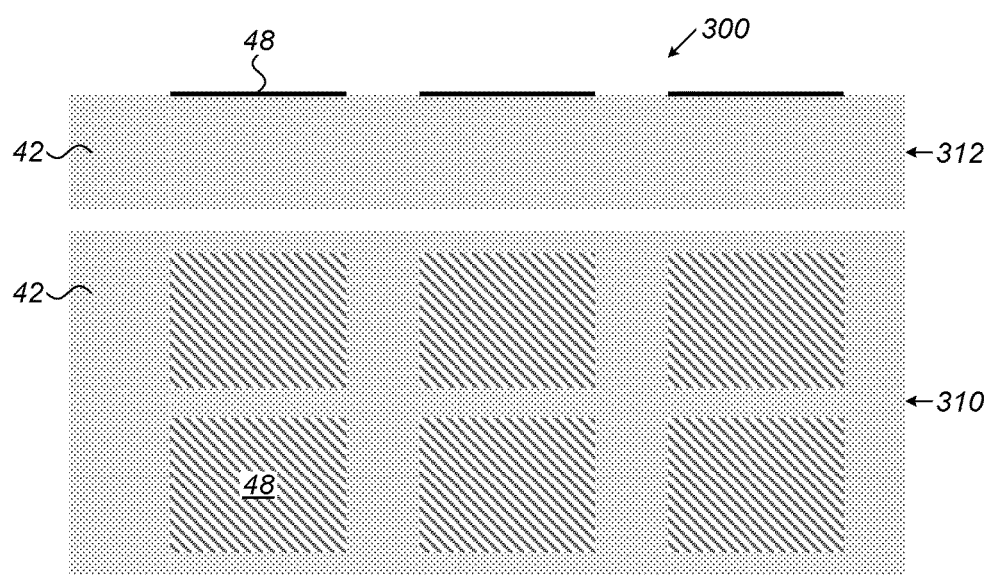
Figure 6B:
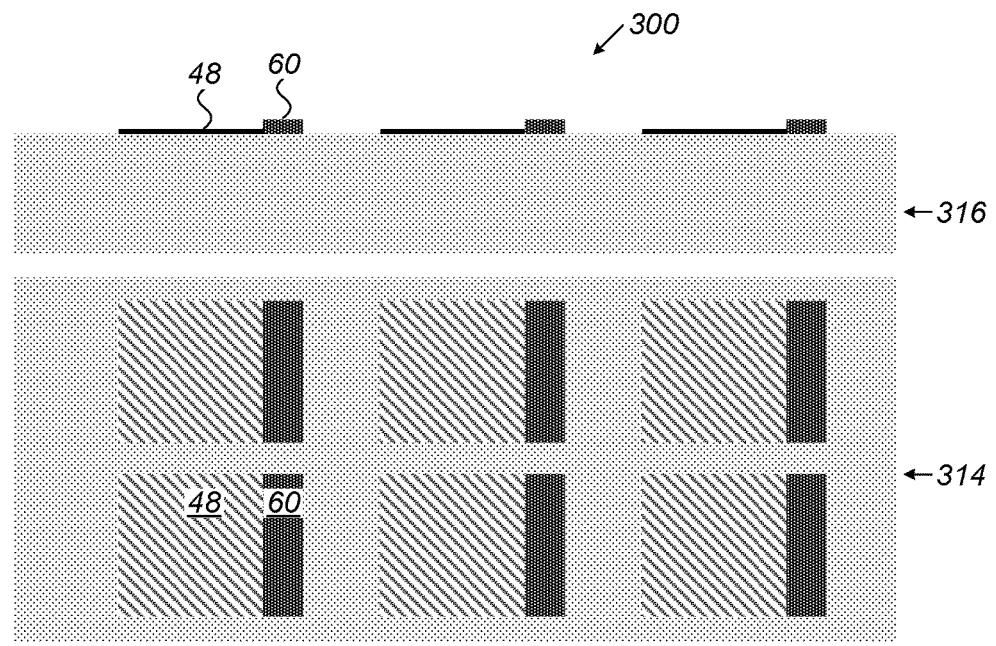
Figure 6C:
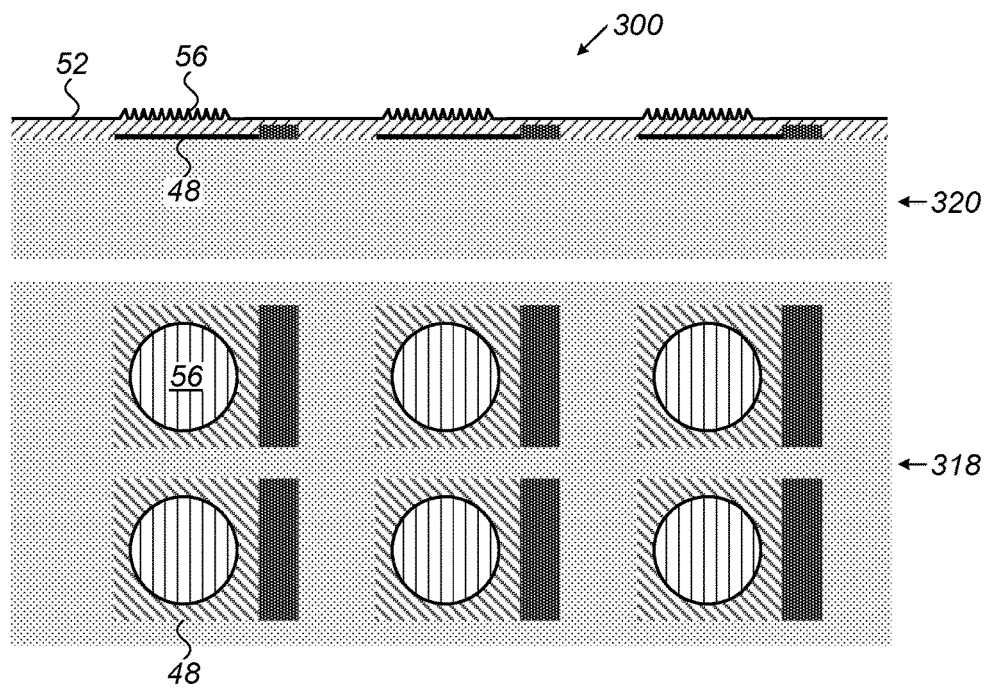
Figure 6D:
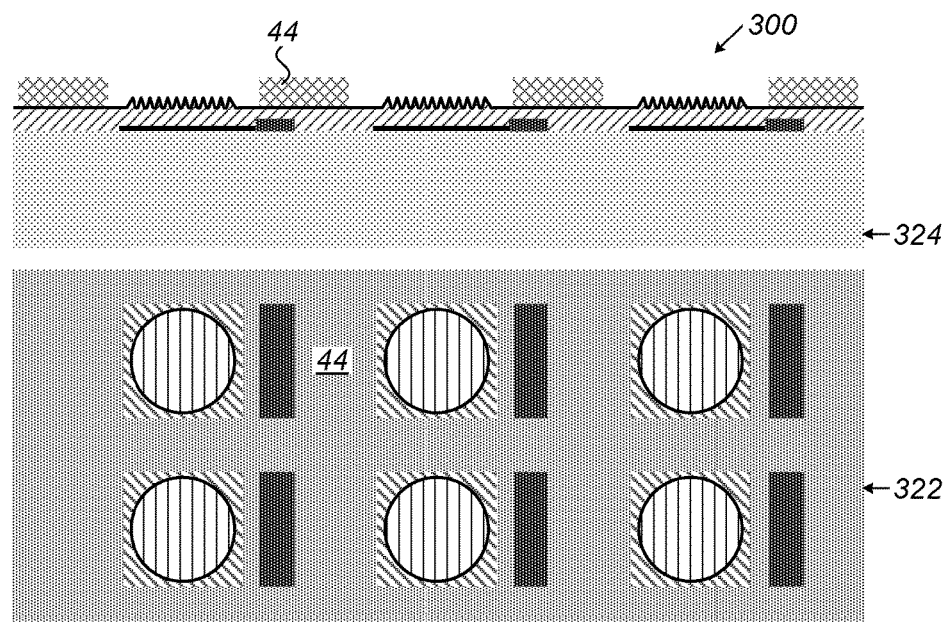
Figure 6E:
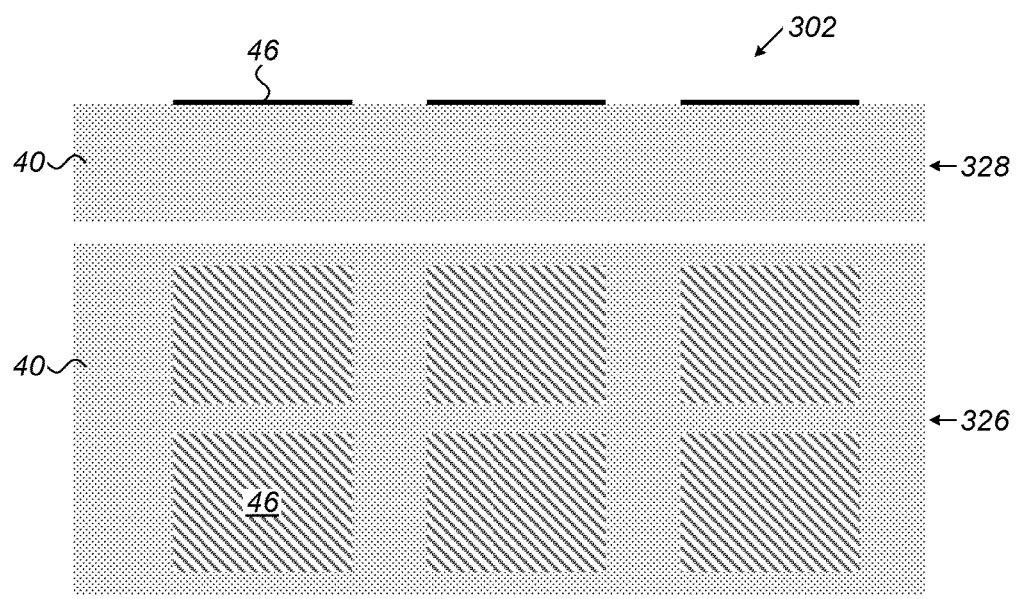
Figure 6F:
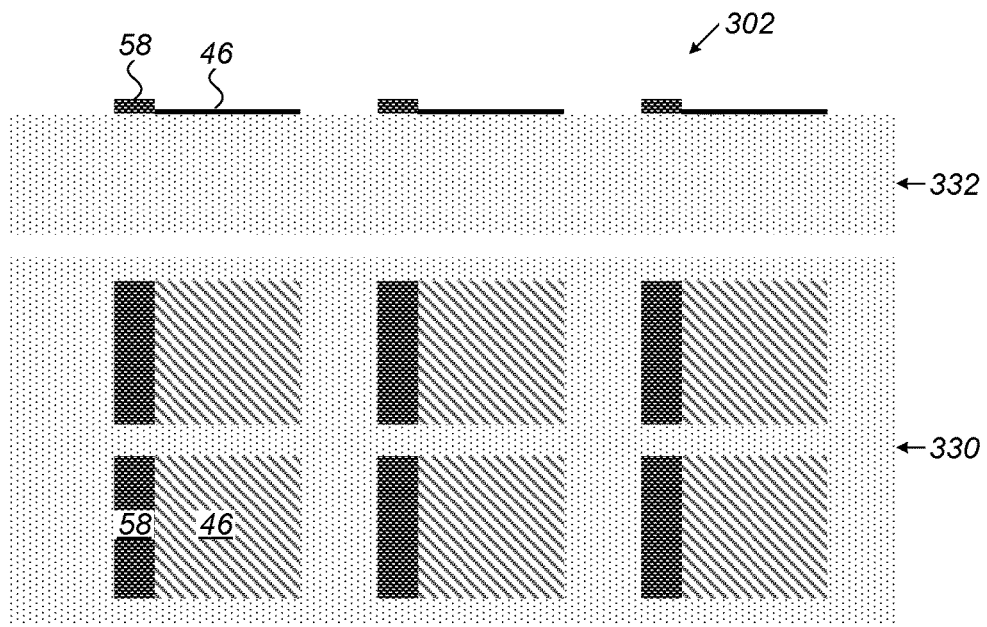
Figure 6G:
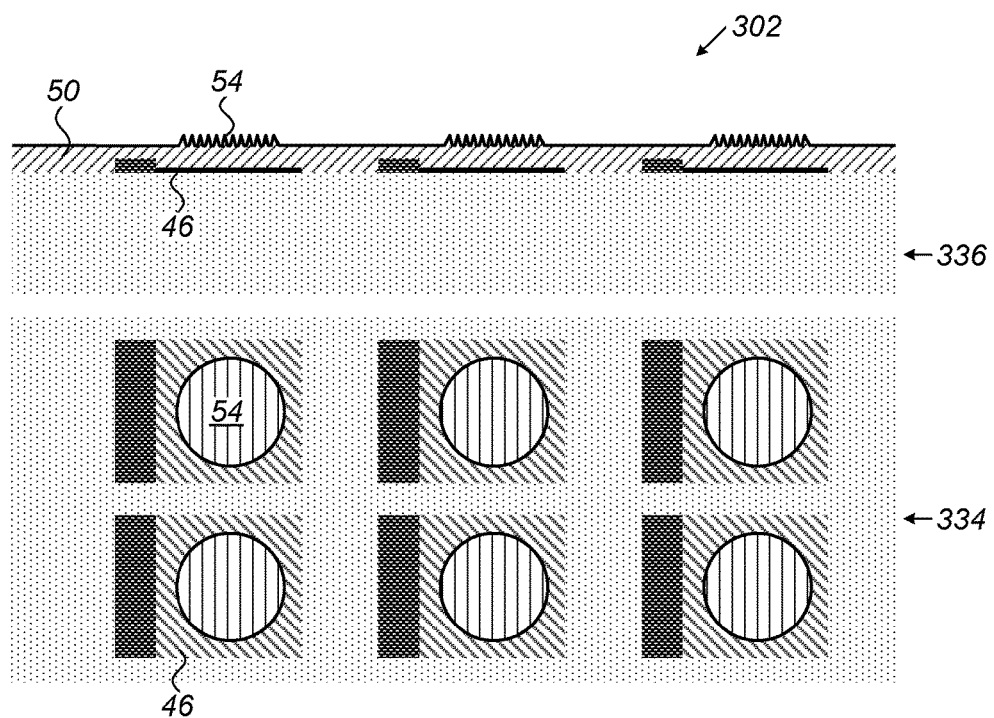
Figure 6J:
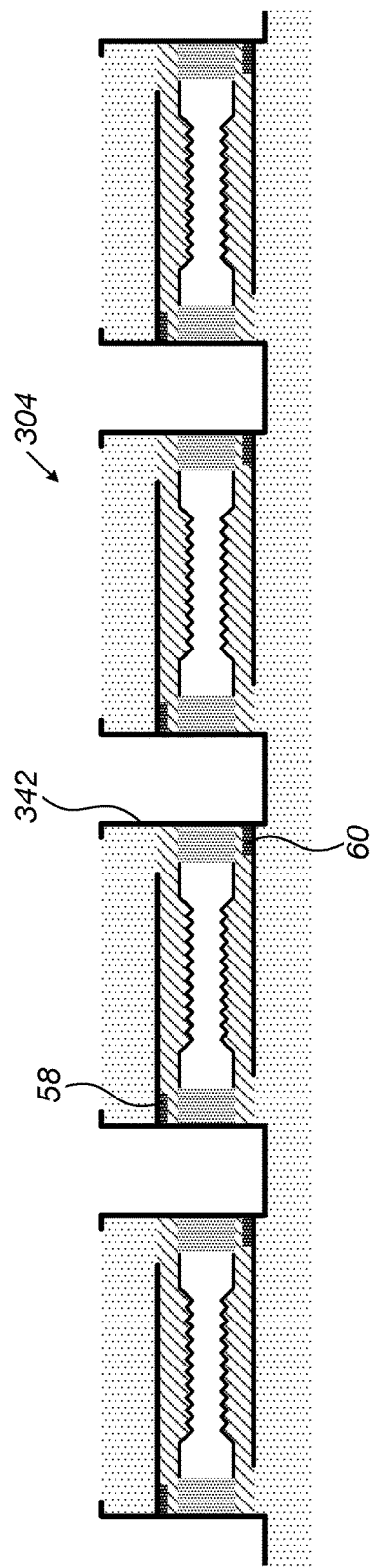
Figure 6K:
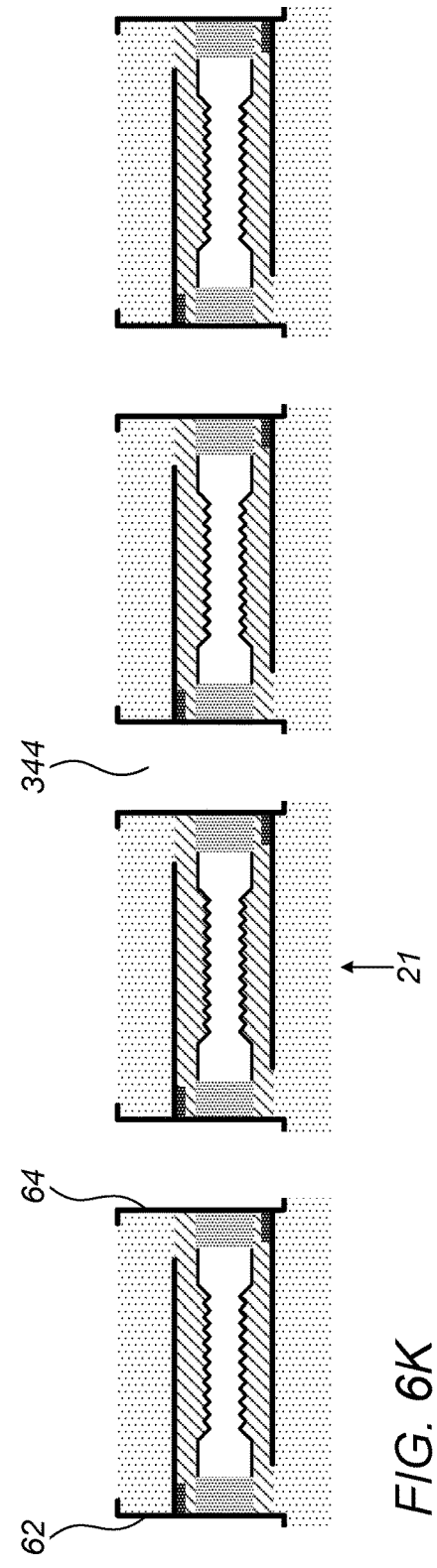

FIGS. 6A-K are schematic top and sectional views showing successive steps in a manufacturing process, wherein first and second capacitance electrodes are deposited between the DOEs and the substrates, according to another embodiment of the invention. In this manufacturing process, whose end result has previously been depicted in FIG. 1B as DOE module 21, two separate assemblies: an assembly 300 and an assembly 302, are built in sequential process steps and subsequently bonded together to an assembly 304. Although assemblies 300, 302, and 304 are modified throughout the process steps, we will again keep this numbering from step to step to facilitate following the process. We will also use, where applicable, labels from FIG. 1B. FIGS. 6A-D are schematic views of coating, patterning, and etching or embossing process steps, performed on assembly 300. FIGS. 6E-G are schematic views of coating, patterning, and etching or embossing process steps, performed on assembly 302. FIGS. 6I-K are schematic views of process steps on assembly 304, after bonding of assemblies 300 and 302 into assembly 304 in FIG. 6H.

FIG. 6A shows a schematic top view 310 and a schematic sectional view 312 of the result of a coating and patterning step on assembly 300. In this process step, second capacitance electrodes 48 are coated and patterned over transparent substrate 42. As in the process steps of FIGS. 5A-K, the patterns form a repeating matrix on the substrates, and the process steps are performed in a parallel fashion to all unit cells of the matrix.

FIG. 6B shows a schematic top view 314 and a schematic sectional view 316 of the result of another coating and patterning step on assembly 300. In this coating and patterning step, conductors 60 are formed, connecting to second capacitance electrodes 48.

FIG. 6C shows a schematic top view 318 and a schematic sectional view 320 of the result of a coating and etching or embossing step on assembly 300. Dielectric film 52 is deposited over assembly 300, followed by etching or embossing DOEs 56 into dielectric film 52, on top of second capacitance electrodes 48.

FIG. 6D shows a schematic top view 322 and a schematic sectional view 324 of the result of another coating and patterning step on assembly 300. In this coating and patterning step spacers 44 are formed. In another embodiment, spacers 44 are etched or embossed into the material of substrate 42.

FIG. 6E shows a schematic top view 326 and a schematic sectional view 328 of the result of a coating and patterning step on assembly 302. In this process step, first capacitance electrodes 46 are coated and patterned over transparent substrate 40.

FIG. 6F shows a schematic top view 330 and a schematic sectional view 332 of the result of another coating and patterning step on assembly 302. In this coating and patterning step, conductors 58 are formed, connecting to first capacitance electrodes 46.

FIG. 6G shows a schematic top view 334 and a schematic sectional view 336 of the result of a coating and etching or embossing step on assembly 302. Dielectric film 50 is deposited over assembly 302, followed by etching or embossing DOEs 54 into dielectric film 50, above first capacitance electrodes 46.

FIG. 6H shows a schematic sectional view of assembly 304 formed by flipping assembly 302 over and bonding it to assembly 300. Assemblies 300 and 302 have been aligned so as to have each DOE 54 in assembly 302 facing DOE 56 in assembly 300.

FIG. 6I shows a schematic sectional view of assembly 304, after a partial dicing that forms cuts 340 between consecutive DOE pairs 54 and 56, exposing ends of conductors 58 and 60.

FIG. 6J shows a schematic sectional view of assembly 304, after metal deposition and patterning, forming metal films 342, connecting to conductors 58 and 60 through their exposed ends.

FIG. 6K shows a schematic sectional view, after dicing cuts 344 have separated assembly 304 into individual DOE modules 21, and have at the same time formed external conductors 62 and 64.

Figure 7:
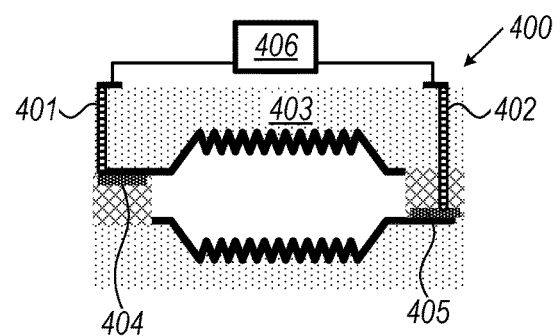
FIG. 7 is a schematic sectional view of a DOE module, in accordance with yet another embodiment of the invention.

FIG. 7 is a schematic view of a DOE module 400 (similar to DOE module 20 of FIG. 1A), in an embodiment wherein external conductors 401 and 402 are formed through vias in a transparent substrate 403, connecting to conductors 404 and 405. Conductors 401 and 402 are further connected to a capacitance measurement circuit 406. Such through-substrate vias may similarly be used in a DOE module similar to DOE module 21 of FIG. 1B.

Figure 8:
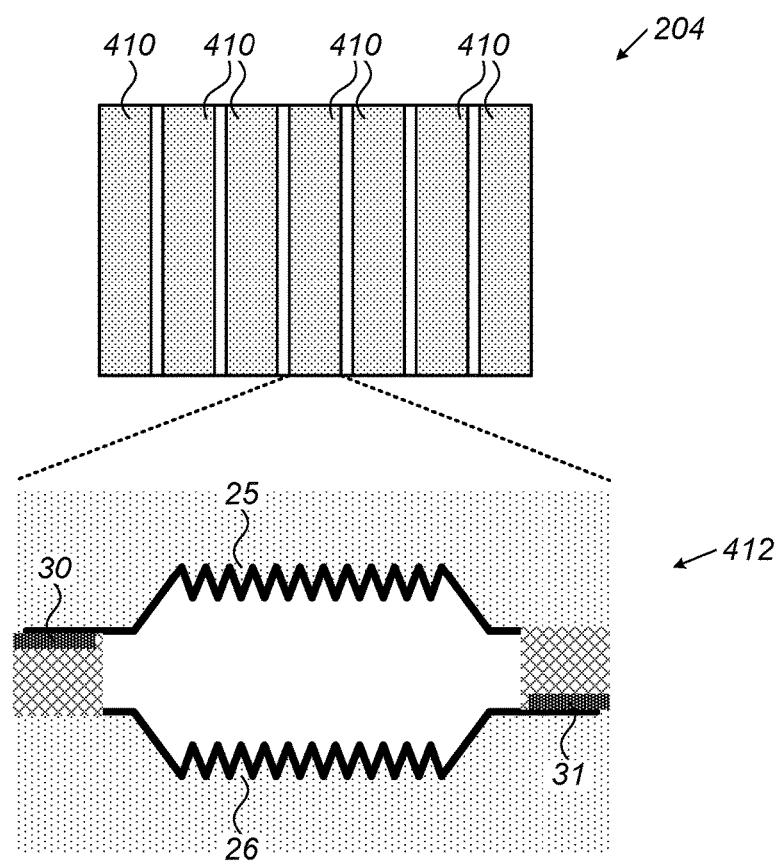
FIG. 8 is a schematic top view of a bonded substrate, cut into strips in preparation for forming electrical connections to a DOE module, in accordance with an embodiment of the invention.
Figure 9A:
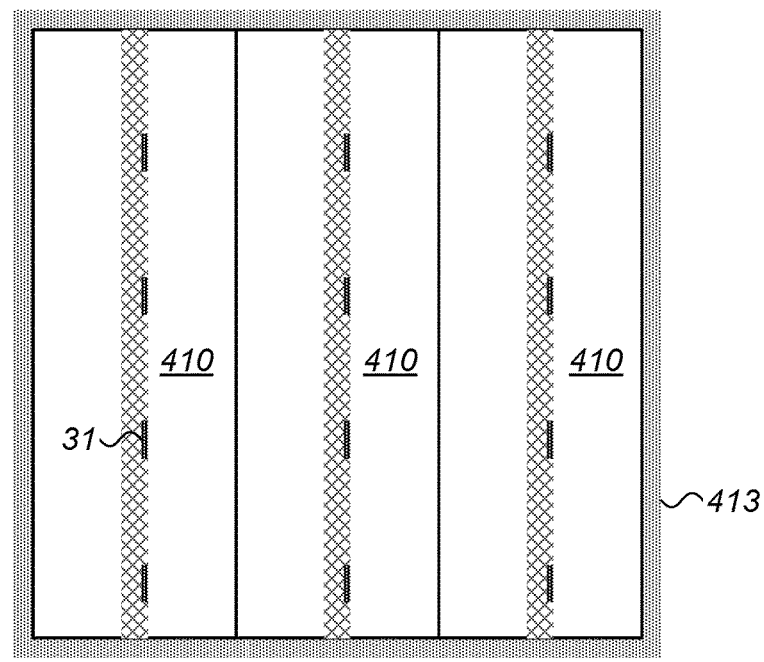
FIGS. 9A-B are schematic top views of rotated strips of bonded substrate on a vacuum chuck, in accordance with an embodiment of the invention.
Figure 9B:
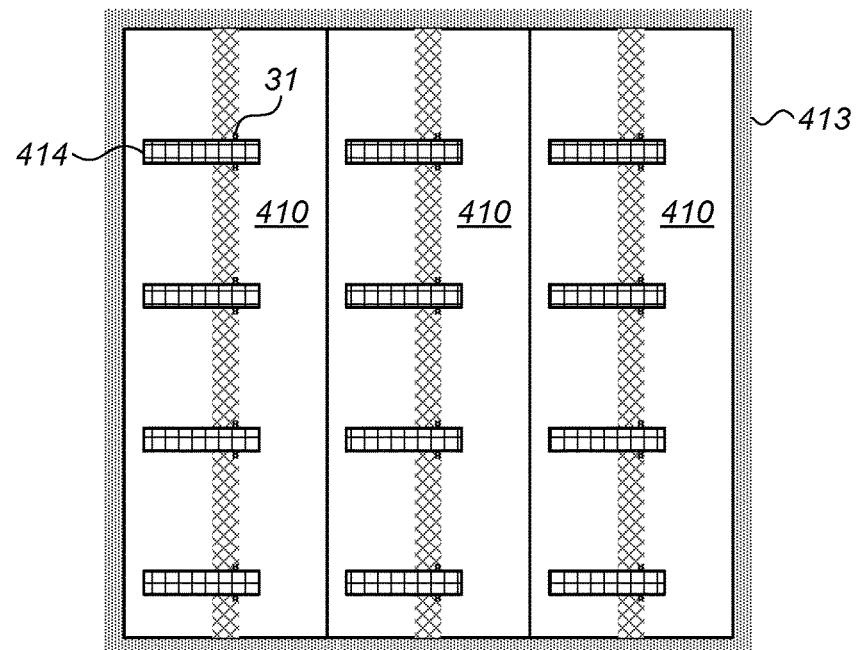

FIGS. 8 and 9A-B are schematic views of a process, wherein external conductors 414 of a DOE module are formed using conductive epoxy, in accordance with an embodiment of the invention. The conductor-forming process shown schematically in FIGS. 8 and 9A-B is based on DOE module 20 of FIG. 1A but may similarly be applied to DOE module 21 of FIG. 1B.

FIG. 8 shows a schematic top view of assembly 204, taken from FIG. 5H, which has now been cut into strips 410, with each strip 410 comprising a single row of pairs of DOEs 25 and 26. An enlarged schematic sectional view 412 across a strip 410 is shown as indicated by the broken lines. Strips 410 have been cut so as to expose ends of conductors 30 and 31.

FIG. 9A shows a schematic view of three strips 410 from FIG. 8, after strips 410 have been turned 90° along their long edges, and stacked side-by-side onto a vacuum chuck 413 below strips 410. The exposed ends of conductors 31 on one side of strips 410 are visible.

FIG. 9B shows a schematic view of strips 410 from FIG. 9A, after conductive epoxy patches 414 have been deposited over exposed sides of strips 410, connecting to conductors 31. In a further, similar process step (not shown), strips 410 are turned by 180° along their long edges, stacked again onto vacuum chuck 413, and additional conductive epoxy patches are deposited over the now visible sides of strips 410, connecting to conductors 30. The strips are then diced to singulate the DOE modules, as described above. Conductive epoxy patches 414 on both sides of the strips are then used for connecting conductors 30 and 31 to a capacitance measurement circuit.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. An optical module, comprising:
   first and second transparent substrates;
   a spacer between the first and second transparent substrates, holding the first transparent substrate in proximity to the second transparent substrate;
   first and second diffractive optical elements (DOEs) on respective faces of the first and second transparent substrates;
   at least first and second capacitance electrodes, disposed respectively on the first and second transparent substrates in proximity to the first and second DOEs; and
   circuitry coupled to measure changes in a capacitance between at least the first and second capacitance electrodes.

2. The optical module according to claim 1, and comprising conductive shielding coatings on one or more outer surfaces of the transparent substrates.

3. The optical module according to claim 1, wherein the first and second capacitance electrodes comprise planar electrodes.

4. The optical module according to claim 1, wherein the first and second capacitance electrodes comprise interdigitated electrodes.

5. The optical module according to claim 1, and comprising electrical conductors comprising conductive epoxy, which are deposited on one or more side surfaces of the transparent substrates and couple the circuitry to the first and second capacitance electrodes.

6. The optical module according to claim 1, and comprising electrical conductors that are deposited inside one or more vias passing through the transparent substrates and couple the circuitry to the first and second capacitance electrodes.

7. The optical module according to claim 1, and comprising at least one additional pair of reference capacitance electrodes in a location insensitive to changes in the DOEs, wherein the circuitry is additionally coupled to the reference capacitance electrodes and is configured to compare the changes measured in the capacitance measured between the first and second capacitance electrodes to a reference capacitance value read from the reference capacitance electrodes.

8. The optical module according to claim 1, wherein the spacer forms a hermetic seal between the first and second transparent substrates.

9. The optical module according to claim 1, wherein the spacer comprises an electrically conductive material, which is connected to ground potential.

10. The optical module according to claim 1, wherein the electrodes are deposited on the respective faces of the substrate, and the DOEs are formed over the electrodes.

11. The optical module according to claim 1, wherein the electrodes are deposited over the DOEs.

* * * * *